United States Patent
Ziv

(10) Patent No.: US 11,286,246 B2
(45) Date of Patent: Mar. 29, 2022

(54) PRO-DRUGS AND RELATED METHODS

(71) Applicant: Aposense LTD., Petach-Tikva (IL)

(72) Inventor: Ilan Ziv, Kfar Saba (IL)

(73) Assignee: Aposense Ltd., Petach-Tikva (IL)

( * ) Notice: Subject to any disclaimer, the term of this patent is extended or adjusted under 35 U.S.C. 154(b) by 0 days.

(21) Appl. No.: 15/745,714

(22) PCT Filed: Jul. 13, 2016

(86) PCT No.: PCT/IL2016/050749
§ 371 (c)(1),
(2) Date: Jan. 18, 2018

(87) PCT Pub. No.: WO2017/017669
PCT Pub. Date: Feb. 2, 2017

(65) Prior Publication Data
US 2018/0208574 A1 Jul. 26, 2018

Related U.S. Application Data

(60) Provisional application No. 62/196,376, filed on Jul. 24, 2015, provisional application No. 62/200,734, filed on Aug. 4, 2015, provisional application No. 62/214,989, filed on Sep. 6, 2015, provisional application No. 62/263,766, filed on Dec. 7, 2015, provisional application No. 62/309,486, filed on Mar. 17, 2016.

(51) Int. Cl.
*C07D 339/08* (2006.01)
*C07C 271/56* (2006.01)
*G01N 30/02* (2006.01)

(52) U.S. Cl.
CPC .......... *C07D 339/08* (2013.01); *C07C 271/56* (2013.01); *G01N 2030/027* (2013.01); *G01N 2560/00* (2013.01)

(58) Field of Classification Search
None
See application file for complete search history.

(56) References Cited

U.S. PATENT DOCUMENTS

| | | | |
|---|---|---|---|
| 6,046,228 | A | 4/2000 | Rice et al. |
| 2004/0110220 | A1 | 6/2004 | Mirkin et al. |
| 2007/0232702 | A1 | 10/2007 | Ziv et al. |
| 2012/0270917 | A1 | 10/2012 | DeGrado et al. |
| 2013/0211055 | A1 | 8/2013 | Raines et al. |

FOREIGN PATENT DOCUMENTS

| | | | | |
|---|---|---|---|---|
| WO | WO 2009148698 | * | 12/2009 | |
| WO | WO 2009148968 | * | 12/2009 | ........... C07D 339/02 |
| WO | WO-2014/088923 | | 6/2014 | |

OTHER PUBLICATIONS

"metabolite-encyclopedia.com", http://www.encyclopedia.com/doc/1E1-metabolit.html, accessed Jan. 25, 2008, based on The Columbia Encyclopedia, Sixth Edition, 2007. (Year: 2007).*
International Search of PCT Application No. PCT/IL16/50749 dated Jan. 5, 2018.

* cited by examiner

*Primary Examiner* — Noble E Jarrell
(74) *Attorney, Agent, or Firm* — Pearl Cohen Zedek Latzer Baratz LLP

(57) ABSTRACT

The invention relates to Pro-drugs, comprising red-ox-sensitive cleavage sites. The compounds may be utilized in medical practice for targeting of si RNA, antisense oligonucleotides or protein-based therapeutics to the cytoplasmatic compartment of cells both in vitro or in vivo, in a subject in need.

2 Claims, 5 Drawing Sheets

PRO-DRUGS AND RELATED METHODS

CROSS-REFERENCE TO RELATED APPLICATIONS

This application is a National Phase Application of PCT International Application No. PCT/IL2016/050749, International Filing Date Jul. 13, 2016, claiming the benefit of US Provisional Application Nos. 62/196,376, filed Jul. 24, 2015, 62/200,734 filed Aug. 4, 2015, 62/214,989 filed Sep. 6, 2015, 62/263,766 filed Dec. 7, 2015 and 62/309,486 filed Mar. 17, 2016, all of which are hereby incorporated by reference.

FIELD OF THE INVENTION

The invention relates to novel pro-drugs, comprising a cleavable group for release of active drugs. The cleavable group comprises novel red-ox sensitive switch moiety (ROSS). The invention also relates to methods for utilization of these ROSS for medical purposes.

BACKGROUND OF THE INVENTION

It is often desirable in medical practice to administer a drug in an inactive form (namely as a "Pro-drug"). Such approach may be useful in improving drug delivery to its target sites, improving drug performance or reducing toxicity. However, the efficacy of such approach also often depends on the ability to incorporate within the pro-drug a moiety to be cleaved at the target sites, thus enabling the release of the drug to exert its pharmacological action.

Many drugs are administered by systemic administration, i.e., intravenously or per os, while their sites of action are within the cytoplasm. Therefore, conceptually, a pro-drug that is inactive in the blood and the extracellular space, but which undergoes subsequent selective cleavage upon passage through cell membranes into the cytoplasm, with release of the pharmaceutically-active drug thereafter, can be highly useful to improve patient care.

One of the hallmarks of the cytoplasm is its reductive environment relative to the extracellular compartment. This reductive environment is enabled, in part, by the high cytoplasmatic concentrations of reduced glutathione (about 5 mM). Respectively, oxidized, disulfide bonds are very rarely found in cytosolic proteins, where most cysteines have their thiol groups reduced, namely, as free thiol groups (—SH). Therefore, it is desirable to have a pro-drug that comprises a red-ox-sensitive moiety, which is stable in the relatively oxidative extracellular environment, while being cleaved at the reductive intracellular cytoplasmatic compartment, thus releasing the pharmacologically-active drug to exert its pharmacological effects.

Pro-drugs comprising disulfide bonds for cleavage within the cytoplasm via reduction of the disulfide moiety have been attempted in the past, and are reported in the scientific literature. However, such strategies cannot avoid involvement of said pro-drugs in non-specific thiol-disulfide exchange reactions. Considering the huge pool of cysteines in extracellular proteins, such non-specific reactions subsequent to systemic administration of a disulfide-containing pro-drug, may lead to generation of cysteine adducts that may inevitably lead to diversion of the administered drug from target to non-target sites, thus substantially reducing its availability to its target sites. In addition, such reactions may generate haptens, namely new immunological determinants, comprising the adducted drug linked to a protein, thus generating new, immunologically-reactive molecules, which may be associated with severe allergic or immune-mediated adverse effects. Consequently, disulfide moieties are not often found in therapeutically-useful drugs. For the several drugs which comprise disulfide moieties and used in clinical practice, warnings of potential immunological/allergic reactions are often added to the drug package inserts, as demanded by the regulatory authorities.

SUMMARY OF THE INVENTION

Embodiments of the invention concern pro-drugs, comprising red-ox sensitive switch moieties (ROSS) that trigger red-ox-dependent molecular cleavage, for release of an active drug in the cytoplasm. In one of its aspects, the core novelty of the invention relates to the unique design of the ROSS, which comprises three structural motifs: (i). a cyclic hydrocarbon disulfide moiety; (ii). an electrophilic moiety (such as carbonyl group), positioned at 5-7 atoms from the sulfur atoms; and (iii). a leaving group, attached to the electrophilic moiety, for example through carbamate, ester or amide bonds. The leaving group may be linked, among others, to a pharmaceutically-active drug. This unique structure, which underlies the design of the Compounds according to Formulae I, II, III, IIIa, IIIb, IV, V, VI or VII of the Invention, leads to the following functional profile: (A). Inhibition of non-specific thiol-disulfide exchange reactions upon systemic administration to the extracellular compartment, due to the strong propensity of the cyclic disulfide moiety to remain closed in an oxidative environment; (B). Efficient reduction of the disulfide bond and ring opening in an ambient reductive environment (as encountered, for example in the cytoplasm); (C). Subsequent nucleophilic attach, exerted by the thiol or thiolate groups on the electrophilic site (e.g., the carbonyl group); and (D). Release of the leaving group, which, when comprising a useful chemical moiety, such as a drug, is now free to exert its pharmacological actions.

Pro-drugs according to embodiments of the invention have a structure, as set forth in general Formula (Ia) or Formula (Ib):

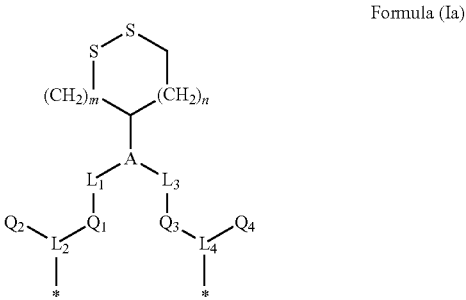

Formula (Ia)

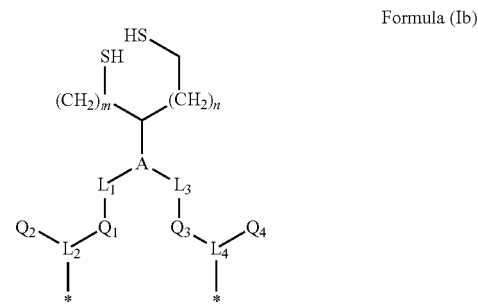

Formula (Ib)

including pharmaceutically acceptable salts, hydrates, solvates and metal chelates of the compounds represented by the structures as set forth in Formula (Ia) or Formula (Ib), and solvates and hydrates of the salts, wherein:

m and n, each stands for an integer, independently selected from 0, 1, 2, 3, 4;

A is selected from null; —CH—, —N—, —CH$_2$—CH—; —CH$_2$—N—; —NH—CH—; —S—CH—; —O—CH—;

Q$_1$, Q$_2$, Q$_3$ or Q$_4$ may be the same or different, and are each independently selected from null, hydrogen, hydroxyl, amine group, a nitro group, a sulfonyl group, a halogen atom, a fluorocarbon group; a carbonyl group —C(=O)—; an amide group [—C(=O)—NH—; —HN—C(=O)—]; —O—C(=O); —C(=O)—O—; a thioester group [—C(=O)—S—; —S—C(=O)—]; a thionoester group —O—C(=S); —C(=S)—O—;

wherein if Q$_1$ is hydrogen, hydroxyl, a nitro group, a sulfonyl group, a halogen atom, or a fluorocarbon group, then Q$_3$ is different from any one of hydrogen, hydroxyl, a nitro group, a sulfonyl group, a halogen atom, or a fluorocarbon group; and wherein if Q$_3$ is hydrogen, hydroxyl, a nitro group, a sulfonyl group, a halogen atom, or a fluorocarbon group, then Q$_1$ is different from any one of hydrogen, hydroxyl, a nitro group, a sulfonyl group, a halogen atom, a fluorocarbon group;

L$_1$, L$_2$, L$_3$ and L$_4$ may be the same or different, and are each independently selected from null, hydrogen, or from the group consisting of:

linear, cyclic or branched C$_1$, C$_2$, C$_3$, C$_4$, C$_5$ alkyl or hetero-alkyl;

linear, cyclic or branched C$_2$, C$_3$, C$_4$, C$_5$, C$_6$, alkylene or heteroalkylene; and C$_5$, C$_6$, C$_7$, C$_8$, C$_9$, C$_{10}$ aryl or heteroaryl;

or any combination thereof;

wherein if L$_1$ is hydrogen, then L$_3$ and L$_4$ are different from hydrogen; and wherein if L$_3$ is hydrogen, than L$_1$ and L$_2$ are different than hydrogen; and wherein if L$_2$ is either null or hydrogen, then L$_4$ is not null or hydrogen; and if L$_4$ is either null or hydrogen then L$_2$ is not null or hydrogen.

* is an optional attachment point of chemical moieties Y and Z, wherein the Pro-drug may include Y or Z or both, and wherein Y and Z each being a subunit of the pro-drug, destined to be separated and released upon its cleavage; and wherein Y and Z may be identical or different. Conceptually, Y or Z can be equal and may be chosen among any chemical moiety known in the art. However, in an embodiment of the invention, either Y or Z or both is a drug, selected from a small-molecule drug, a peptide, a protein and an oligonucleotide, selected from a single-stranded or a double-stranded, natural or modified RNA or DNA. In another embodiment, either Y or Z or both can also be a supportive moiety (SM), as defined below, being a chemical group, that upon its conjugation to the Pro-drug, entails beneficial effects on drug performance in one or more aspects, such as, but not limited to, trans-membrane delivery, targeting to specific tissues, pharmacokinetics, stability or safety.

In an embodiment of the invention, the ROSS comprises the structure as set forth in Formula (IIIa), or its related reduced analogue with free thiol groups:

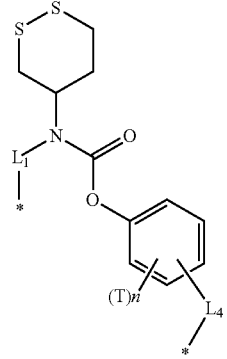

Formula (IIIa)

including pharmaceutically acceptable salts, hydrates, solvates and metal chelates of the compound represented by the structure as set forth in Formula (IIIa), and solvates and hydrates of the salts; L$_1$, L$_4$ and * each has the same meaning as above; n is an integer selected from 0, 1, 2, 3, 4; if n is 1 or more, then each T groups are independently selected from hydroxyl, amine group, a nitro group, a sulfonyl group, a halogen atom or a fluorocarbon group.

In another embodiment, the invention discloses a method for redox-dependent cleavage of a Pro-drug, said method comprising (i). Incorporation in the Pro-drug, a ROSS according to the invention; (ii). Maintaining the Pro-drug initially in an oxidative environment. In such conditions, the ROSS is intact, and thus the pro-drug is not cleaved; (iii). Transferring the Pro-drug to an ambient reductive environment. In such conditions, the ROSS, and thereby also the pro-drug will undergo cleavage, with release of the Y and Z subunits of the Pro-drug.

In yet another embodiment, the invention discloses a method for selective cleavage of a Pro-drug in the cytoplasm of cells, the method comprising: contacting the cells with a Pro-drug of the invention. This will lead to entry of the Pro-drug into the cell followed by selective cleavage of the Pro-drug, due to its ROSS, in the cytoplasm, in response to the reductive ambient conditions in the cytoplasm, dictated, at least in part, by the high local concentrations of glutathione. The cells can be cells in cell culture grown in vitro, or in vivo within a living animal or a human subject.

Another embodiment of the invention relates to a method for treating a medical disorder, the method comprising: administrating to a patient in need, a pharmaceutical composition comprising adequate amounts of a Pro-drug according to the invention.

BRIEF DESCRIPTION OF THE FIGURES

The invention will now be described in connection with certain Examples and embodiments, in a non-limiting manner, with reference to the following illustrative Figures, so that it can be more fully understood. In the drawings.

DETAILED DESCRIPTION OF THE INVENTION

Figure 1:
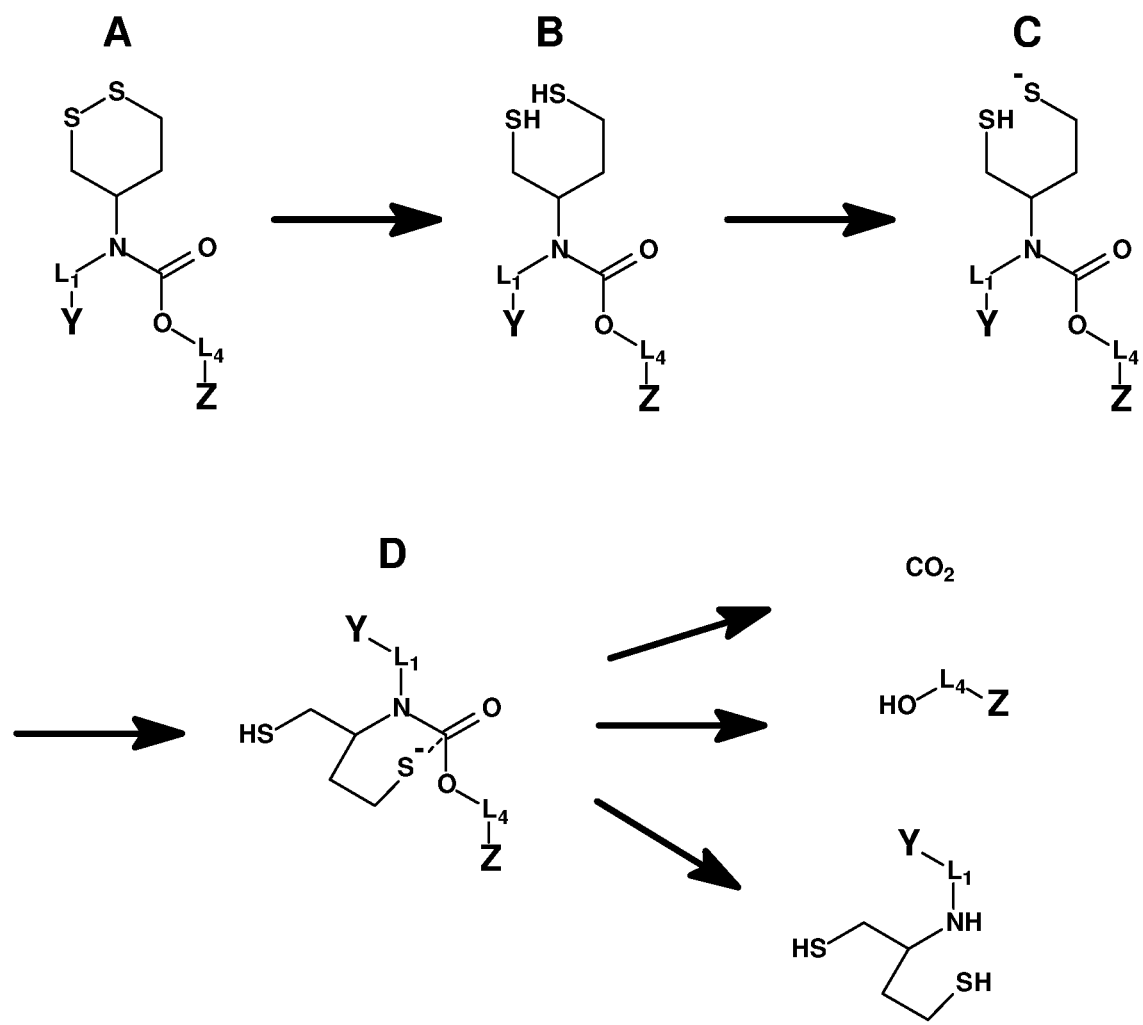
FIG. 1 describes the cleavage of a Pro-drug by ROSS, and the release of the active drug according to embodiments of the invention, wherein the Pro-drug comprises a carbamate moiety (according to Formula III).

Embodiments of the invention concern novel pro-drugs, comprising red-ox sensitive switch moieties (ROSS), that undergo red-ox-dependent cleavage, leading to release of an active drug, to exert its pharmacological action.

In one of its aspects, the invention concerns novel pro-drugs, comprising red-ox sensitive switch moiety (ROSS) that triggers red-ox-dependent molecular cleavage, for release of an active drug in the cytoplasm of a cell. The ROSS comprises three structural motifs: (i). A cyclic hydrocarbon disulfide moiety; (ii). An electrophilic moiety (such as carbonyl group), positioned at a distance of 5-7 atoms from at least one of the sulfur atoms; and (iii). A leaving group, attached to the electrophilic moiety, for example through carbamate, ester or amide bonds. This unique structure, which underlies the design of the Compounds according to Formulae I, II, III, IIIa, IIIb, IV, V, VI or VII of the Invention, leads in some embodiments to the one or more of the following functional results: (A). Inhibition of non-specific thiol-disulfide exchange reactions upon systemic administration to the subject due to the strong propensity of the cyclic disulfide moiety to remain closed in an oxidative environment; (B). Reduction of the disulfide bond, and ring opening in an ambient reductive environment (as encountered, for example in the cytoplasm); (C). Subsequent nucleophilic attach, exerted by the thiol or thiolate groups on the electrophilic site, accurately positioned at a 5-7 atom distance from a sulfur atom, a distance that is adequate for a 5-7 ring-closure upon formation of a tetrahydral intermediate; and (D). Release of the leaving group, which, when chemical moiety, such as a drug, is now free to exert its pharmacological actions.

The term "Pro-drug" in the context of the present invention, relates to a conjugate, comprising two chemical moieties (subunits), and a red-ox sensitive switch moiety of the invention (ROSS). Linkage between the subunits is either directly, or through linker(s) groups [for example L moiety (ies)]. The subunits of the Pro-drug can be various chemical moieties. Preferably, one of the subunits is a drug. Linkage between the subunits can be through any means known in the art, including spacers, and can be performed via covalent, electrostatic, coordinative bonds, or combinations thereof.

The term "drug" in the context of the present invention, relates to a chemical moiety, capable of exerting a pharmacological beneficial effect, being either inhibition of a disease process, cure of a disease, or amelioration of disease symptoms or signs. The drug may be a small-molecule drug, or a macromolecule drug, such as a peptide, protein or oligonucleotide (e.g., single-stranded or double-stranded, RNA or DNA). In a specific embodiment of the invention, the oligonucleotide can be RNA strands for gene silencing, i.e., siRNA (small interfering RNA), or DNA sequences, designed to serve as antisense oligonucleotides (ASO).

The term "red-ox sensitive switch moiety (ROSS)" in the context of present invention, relates to a chemical group, that when incorporated within a Pro-drug, undergoes red-ox-dependent cleavage, enabling separation and release of the subunits of the Pro-drug. Specifically, ROSSs of the invention relate to chemical moieties, manifesting stability in an oxidative environment, such as that encountered in the extracellular space, while undergoing cleavage in reductive conditions, such as those encountered in the cytoplasm.

The term supportive moiety (SM) in the context of the invention, refers to a chemical group of a Pro-drug, entailing beneficial effects on drug performance in one or more aspects, such as, but not limited to, trans-membrane delivery, targeting to specific tissues, pharmacokinetics, stability or safety.

The term "linker(s)" (L moieties) in the context of invention, relates to a chemical group, linking subunits of the pro-drug. Linkage can be through any means known in the art, including spacers, and can be performed via covalent, electrostatic, coordinative bonds, or combinations thereof.

The term "heteroalkyl, heteroalkylene or heteroaryl" in the context of the invention, relates to the respective hydrocarbon structure, wherein a least one of the atoms has been replaced by a nitrogen, oxygen, or sulfur atom(s).

Pro-drugs according to embodiments of the invention comprise a ROSS, having the a structure, as set forth in general Formula (Ia) or Formula (Ib):

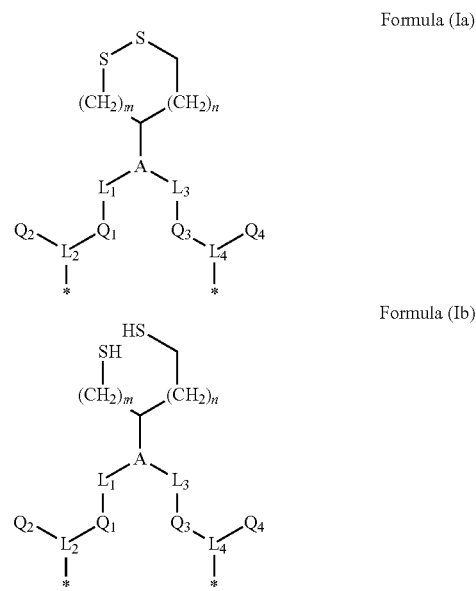

Formula (Ia)

Formula (Ib)

including pharmaceutically acceptable salts, hydrates, solvates and metal chelates of the compounds represented by the structures as set forth in Formula (Ia) or Formula (Ib), and solvates and hydrates of the salts, wherein:

m and n, each stands for an integer, independently selected from 0,1,2,3,4;

A is selected from null; —CH—, —N—, —CH$_2$—CH—; —CH$_2$—N—; —NH—CH—; —S—CH—; —O—CH—;

Q$_1$, Q$_2$, Q$_3$ or Q$_4$ may be the same or different, and are each independently selected from null, hydrogen, hydroxyl, amine group, a nitro group, a sulfonyl group, a halogen atom, a fluorocarbon group; a carbonyl group —C(=O)—; an amide group [—C(=O)—NH—;

—HN—C(=O)—]; —O—C(=O); —C(=O)—O—; a thioester group [—C(=O)—S—; —S—C(=O)—]; a thionoester group —O—C(=S); —C(=S)—O—;

wherein if $Q_1$ is hydrogen, hydroxyl, a nitro group, a sulfonyl group, a halogen atom, or a fluorocarbon group, then $Q_3$ is different from any one of hydrogen, hydroxyl, a nitro group, a sulfonyl group, a halogen atom or a fluorocarbon group; and wherein if $Q_3$ is hydrogen, hydroxyl, a nitro group, a sulfonyl group, a halogen atom or a fluorocarbon group, then $Q_1$ is different from any one of hydrogen, hydroxyl, a nitro group, a sulfonyl group, a halogen atom, a fluorocarbon group;

$L_1$, $L_2$, $L_3$ and $L_4$ may be the same or different, and are each independently selected from null, hydrogen, or from the group consisting of:

linear, cyclic or branched $C_1$, $C_2$, $C_3$, $C_4$, $C_5$ alkyl or hetero-alkyl;

linear, cyclic or branched $C_2$, $C_3$, $C_4$, $C_5$, $C_6$, alkylene or heteroalkylene; and $C_5$, $C_6$, $C_7$, $C_8$, $C_9$, $C_{10}$ aryl or heteroaryl;

wherein if $L_1$ is hydrogen, then $L_3$ and $L_4$ are different than hydrogen; and wherein if $L_3$ is hydrogen, than $L_1$ and $L_2$ are different than hydrogen;

and wherein if $L_2$ is either null or hydrogen, then $L_4$ is not null or hydrogen; and if $L_4$ is either null or hydrogen, then $L_2$ is not null or hydrogen.

is an optional attachment point of chemical moieties Y and Z, wherein Y and Z each being a subunit of the pro-drug, destined to be separated and released upon its cleavage; and wherein Y and Z may be identical or different.

Conceptually, Y or Z or both can be chosen among any chemical moiety known in the art. However, in a preferred embodiment, either Y or Z is a drug, selected from a small-molecule drug, a peptide, a protein and an oligonucleotide, selected from a single-stranded or a double-stranded, natural or modified RNA or DNA. In another embodiment, either Y or Z can also be a supportive moiety (SM), as defined below, being a chemical group, that upon its conjugation to the Pro-drug, entails beneficial effects on drug performance in one or more aspects, such as, but not limited to, trans-membrane delivery, targeting to specific tissues, pharmacokinetics, stability or safety.

In one embodiment, the Pro-drug of the Invention comprises a ROSS, having the structure as set forth in the general Formula (IIIa) or Formula (IIIb):

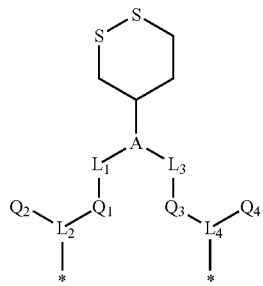

Formula (IIa)

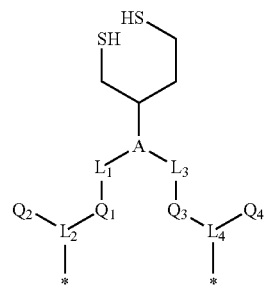

Formula (IIb)

including pharmaceutically acceptable salts, hydrates, solvates and metal chelates of the compound represented by the structure as set forth in Formula (IIIa) or Formula (IIIb), and solvates and hydrates of the salts; wherein A, $Q_1$, $Q_2$, $Q_3$, $Q_4$, $L_1$, $L_2$, $L_3$, $L_4$ and * all have the same meaning as above.

In an embodiment, the ROSS comprises the structure as set forth in Formula (III) or its related reduced analogue with free thiol groups:

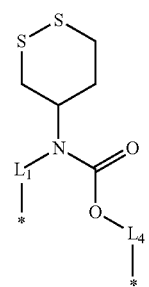

Formula (III)

including pharmaceutically acceptable salts, hydrates, solvates and metal chelates of the compound represented by the structure as set forth in Formula (III), and solvates and hydrates of the salts; *, $L_1$ and $L_4$ each has the same meaning as above.

In an embodiment, the ROSS comprises the structure as set forth in Formula (IIIa), or its related reduced analogue with free thiol groups:

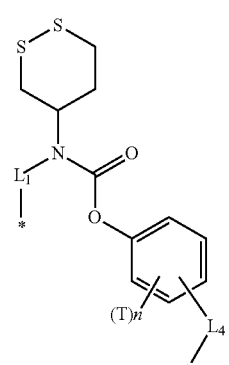

Formula (IIIa)

including pharmaceutically acceptable salts, hydrates, solvates and metal chelates of the compound represented by the structure as set forth in Formula (IIIa), and solvates and hydrates of the salts; $L_1$, $L_4$ and * each has the same meaning as above; n is an integer selected from 0, 1, 2, 3, 4; if n is more than 1, then each T is independently selected from hydroxyl, amine group, a nitro group, a sulfonyl group, a halogen atom or a fluorocarbon group.

In another embodiment, the ROSS comprises the structure as set forth in Formula (IIIb), or its related reduced analogue with free thiol groups:

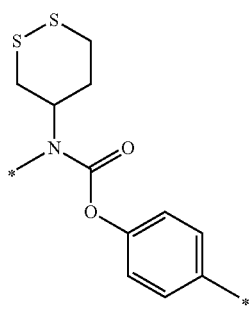

Formula (IIIb)

including pharmaceutically acceptable salts, hydrates, solvates and metal chelates of the compound represented by the structure as set forth in Formula (IIIb), and solvates and hydrates of the salts; each * has the same meaning as above.

In another embodiment, the ROSS comprises the structure as set forth in Formula (IV), or its related reduced analogue with free thiol groups:

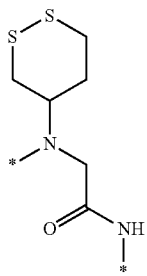

Formula (IV)

including pharmaceutically acceptable salts, hydrates, solvates and metal chelates of the compound represented by the structure as set forth in Formula (IV), and solvates and hydrates of the salts; each * has the same meaning as above.

In another embodiment, the ROSS comprises the structure as set forth in Formula (V) or its related reduced analogue with free thiol groups:

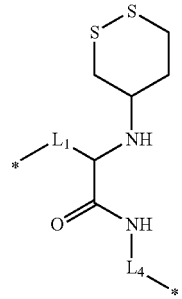

Formula (V)

including pharmaceutically acceptable salts, hydrates, solvates and metal chelates of the compound represented by the structure as set forth in Formula (V), and solvates and hydrates of the salts; * , $L_1$ and $L_4$ each having the same meaning as above. In another more embodiment, the ROSS comprises the structure as set forth in Formula (VI) or its related reduced analogue with free thiol groups:

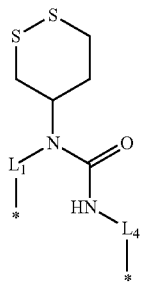

Formula (VI)

including pharmaceutically acceptable salts, hydrates, solvates and metal chelates of the compound represented by the structure as set forth in Formula (VI), and solvates and hydrates of the salts; *, $L_1$ and $L_4$ each has the same meaning as above. In another more specific embodiment, the ROSS comprises the structure as set forth in Formula (VII) or its related reduced analogue with free thiol groups:

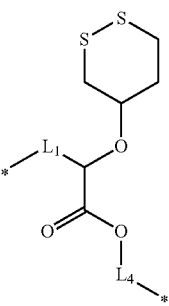

Formula (VII)

including pharmaceutically acceptable salts, hydrates, solvates and metal chelates of the compound represented by the structure as set forth in Formula (VII), and solvates and hydrates of the salts; *, $L_1$ and $L_4$ each has the same meaning as above.

Embodiments of the invention provide novel pro-drugs, comprising a ROSS, having the structure as set forth in any of Formulae I, II, III, IIIa, IIIb, IV, V, VI or VII, in either the oxidized or reduced forms, and respective pharmaceutical compositions, comprising the pro-drugs and pharmaceutically-acceptable carrier(s) or salt(s). The pharmaceutical compositions may be administered either locally or systemically, for example, per os, or by injection.

In an embodiment of the Invention, there is provided a method for redox-dependent cleavage of a Pro-drug, the method comprising (A). Incorporation of a ROSS in the structure of the Pro-drug, wherein the ROSS has the following structural motifs: (i). a cyclic hydrocarbon disulfide moiety; (ii). A carbonyl group, positioned at 5-7 atoms from at least one of the sulfur atoms; and (iii). A leaving group, attached to the carbonyl group through carbamate, ester or amide bonds; (B). Maintaining the Pro-drug initially in an oxidative environment; and (C). Transferring the Pro-drug into an ambient reductive environment, thereby providing conditions for pro-drug cleavage and release the active drug.

In a related embodiment of the invention, it concerns a method for redox-dependent cleavage of a Pro-drug, said method comprising (A). Incorporation in the structure of the Pro-drug a ROSS according to any of Formulae I, II, III, IIIa, IIIb, IV, V, VI or VII; (B). Maintaining the Pro-drug initially in an oxidative environment. In such conditions, the ROSS is intact, and thus the Pro-drug is not cleaved; (C). Exposing the Pro-drug to an ambient reductive environment. In such conditions, the ROSS, and thereby also the pro-drug will undergo cleavage, with release of the Y and Z subunits of the Pro-drug.

In yet another embodiment, the Invention discloses a method for selective cleavage of a Pro-drug in the cytoplasm of cells, said method comprising: (A). Contacting the cells with a Pro-drug of the invention, comprising a ROSS according to any Formulae I, II, III, IIIa, IIIb, IV, V, VI or VII; The Pro-drug will enter into the cells. Due to the reductive ambient conditions in the cytoplasm, selective cleavage of the ROSS will then take place.

Other embodiments of the invention disclose methods for treatment of medical disorders, based on the above pharmaceutical compositions. The medical treatment comprises the administration to a patient in need, adequate amounts of a pharmaceutical composition, comprising a ROSS according to any of Formulae Formulae I, II, III, IIIa, IIIb, IV, V, VI or VII, linked to a drug useful for the treatment of the respective medical disorder.

Embodiments of the invention include a method for medical treatment with siRNA, ASO or a therapeutic protein; the method comprising the administration to a patient in need, a pharmaceutical composition, comprising adequate amounts of a Pro-drug of the invention, comprising a structure as set forth in any of Formulae I, II, III, IIIa, IIIb, IV, V, VI or VII, linked to siRNA, an ASO or a therapeutic protein, useful in inhibiting disease-related processes in the specific patient.

Another embodiment of the invention relates to a therapeutic protein, administered as a replacement therapy. Such replacement therapy may be needed in the treatment of a disease, associated with reduced levels of a physiologically-important protein, due to its deficiency or mutations. In such case, the respective protein may be delivered exogenously, as a drug.

In another embodiment, either Y or Z or both Y and Z may be a drug, being a protein that has as role in gene regulation, including, among others, proteins that have a role in DNA or RNA editing (adding, disrupting or changing the sequence of specific genes). In one embodiment, the protein may be a member of the CRISPRs (clustered regularly interspaced short palindromic repeats)-related proteins. Specifically, the protein can be or may comprise the Cas9 protein (CRISPR associated protein 9), an RNA-guided DNA nuclease enzyme, or an analogue thereof.

In a related embodiment of the invention, the Invention concerns a method for genetic treatment of a medical disorder, the method comprising administration to a patient in need, therapeutically effective amounts of a pharmaceutical composition, comprising a Pro-drug according to any of Formulae I, II, III, IIIa, IIIb, IV, V, VI or VII, where either Y or Z is a CRISPR protein, such as Cas9, administered together with an appropriate guide oligonucleotide, thus achieving delivery of said protein, loaded with a respective guide oligonucloetide into the cells, where they can exert their genome editing activity. A guide oligonucloetide, in this context, is a sequence of RNA or DNA that guides the Cas9 protein to a specific locus on the DNA, in order to induce a double-strand DNA cleavage at that site, thus enabling to repair a local defect in the genetic material. In the case of Cas9, the guide oligonucleotide is RNA.

Therefore, pro-drugs according to embodiments of the invention, and the respective pharmaceutical compositions and methods, may be beneficial, among others, in treatment of medical disorders, selected, among others, from cancer, toxic insults, ischemic disease, infectious disease, protein storage disease, trauma, immune-mediated disease, or a degenerative disease.

In the field of neurological disorders, conjugates according to embodiments of the invention may be useful, among others, for the treatment of neurodegenerative disorders, such as Alzheimer's disease, Motor Neuron Disease, Parkinson's disease, Huntington's disease, multiple sclerosis and Creutzfeldt-Jacob disease.

According to some embodiments, the medical disorder is cancer. As used herein, the term "cancer" refers to the presence of cells possessing characteristics, typical of cancer-causing cells, such as uncontrolled proliferation, loss of specialized functions, immortality, significant metastatic potential, significant increase in anti-apoptotic activity, rapid growth and proliferation rate, and certain characteristic morphology and cellular markers. Typically, cancer cells are in the form of a tumor, existing locally within an animal, or circulating in the bloodstream as independent cells, as are, for example, leukemic cells.

EXAMPLES

Some examples will now be described, in order to further illustrate the invention, and to demonstrate, in a non-limiting manner, how embodiments of the invention may be carried-out in practice.

Figure 2:
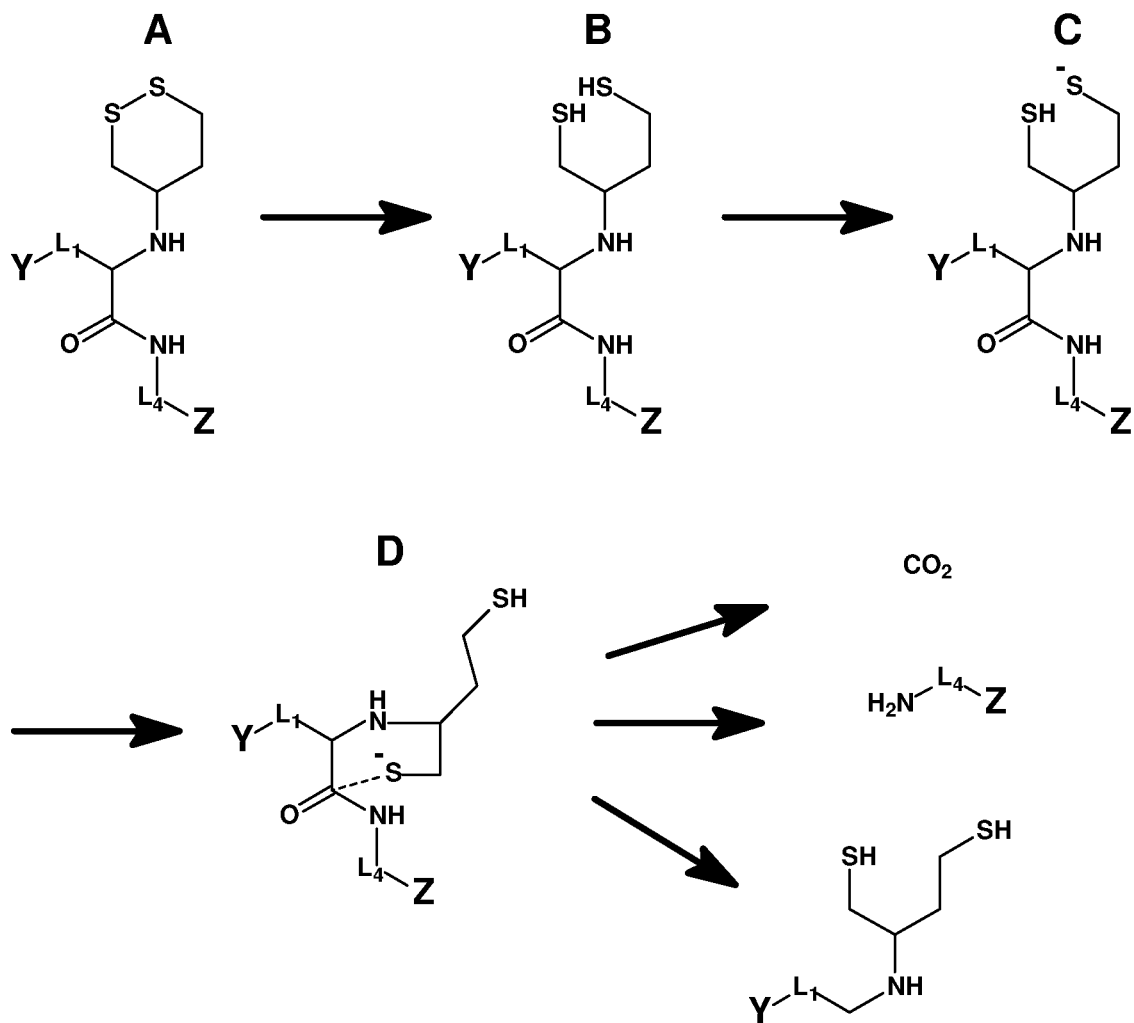
FIG. 2 describes the cleavage of a Pro-drug by ROSS, and the release of the active drug according to embodiments of the invention, wherein the Pro-drug comprises an amide moiety (according to Formula V).
Figure 3:
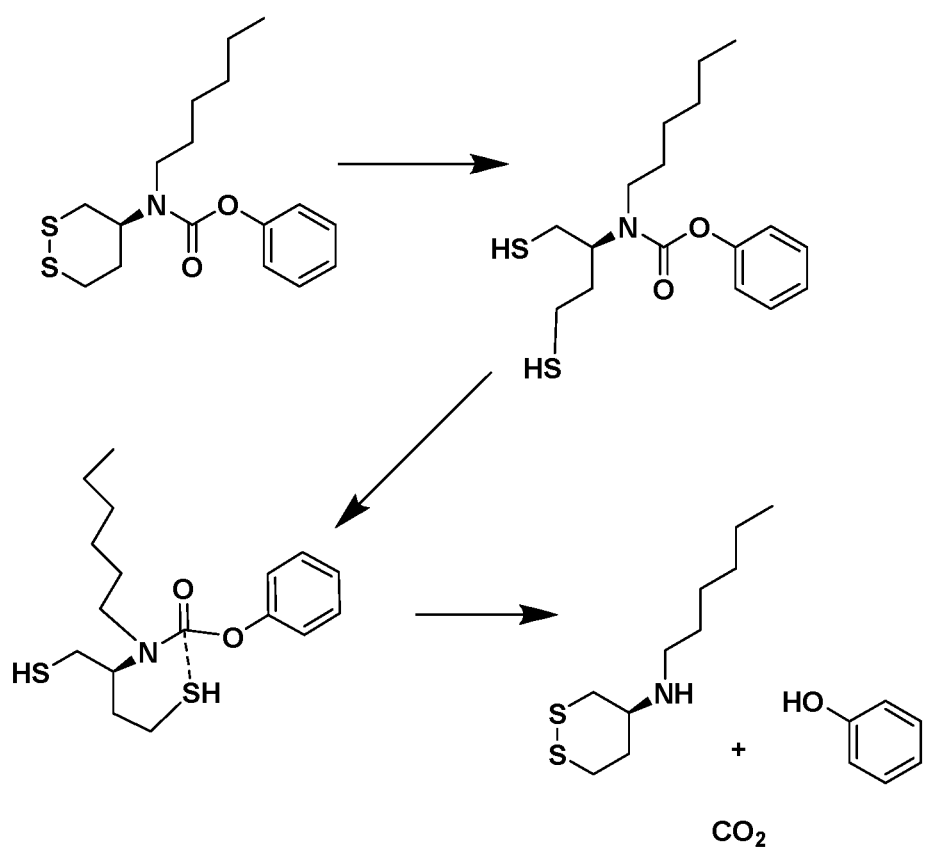
FIG. 3 describes the cleavage of a Pro-drug by ROSS, according to embodiments of the invention (according to Formula IIIb).

Example 1: A Potential Mechanism of Action of Pro-Drugs According to Embodiments of the Invention The action of the Pro-drugs according to embodiments of the invention involves several steps, described in FIG. 1, FIG. 2, FIG. 3, exemplifying structures according to Formula (III), having a carbamate moiety; and Formulae (IV) or (V), comprising an amide moiety. In the described pro-drugs, Y is siRNA, and Z is, for example, a moiety for delivery of the pro-drugs across phospholipid membranes.

1. The Pro-drug is administered in its cyclic, oxidized form (A). Administration can be systemic, via oral or intravenous routes. The extracellular space is characterized by a relative oxidative environment. Therefore, during the distribution of the drug in this compartment, it maintains the oxidized conformation according to FIG. 1A and FIG. 2A. Due to its cyclic 6-member ring structure, in case of occasional nucleophilic attack of the disulfide bond by a thiol or thiolate group of a protein, the Pro-drug will predominantly manifest internal ring closure, over generation of disulfide adducts with the neighboring thiols.

2. Due to the activity of the Z moiety, the Pro-drug passes through the cell membrane into the cytoplasm. Once within the cytoplasm, due to the ambient reductive environment, the S—S bond is reduced to free-thiol (—SH) groups (B).
3. Respective of the pKa values of the thiol groups (about 8 and 9), a small fraction of molecules will have one of its thiol groups de-protonated in physiological pH, to yield a thiolate anion (C).
4. The thiol or the respective thiolate anion are conveniently-positioned (at the $6^{th}$ atom position) to perform an intramolecular nucleophilic attack on the carbonyl of the carbamate or amide groups (D).
5. Consequently, there is formation of a tetrahedral intermediate, followed by cleavage and release of the leaving group.

Example 2: A Method for Synthesis of a Pro-Drug According to Formula III

Synthesis is performed according to the following Scheme 1, while isocyanate 11 is synthesized according to Scheme 2. Intermediate 1 is prepared according to Scheme 3, starting from commercially-available estradiol. 2-amino-1,4-dithio-butane is also commercially-available.

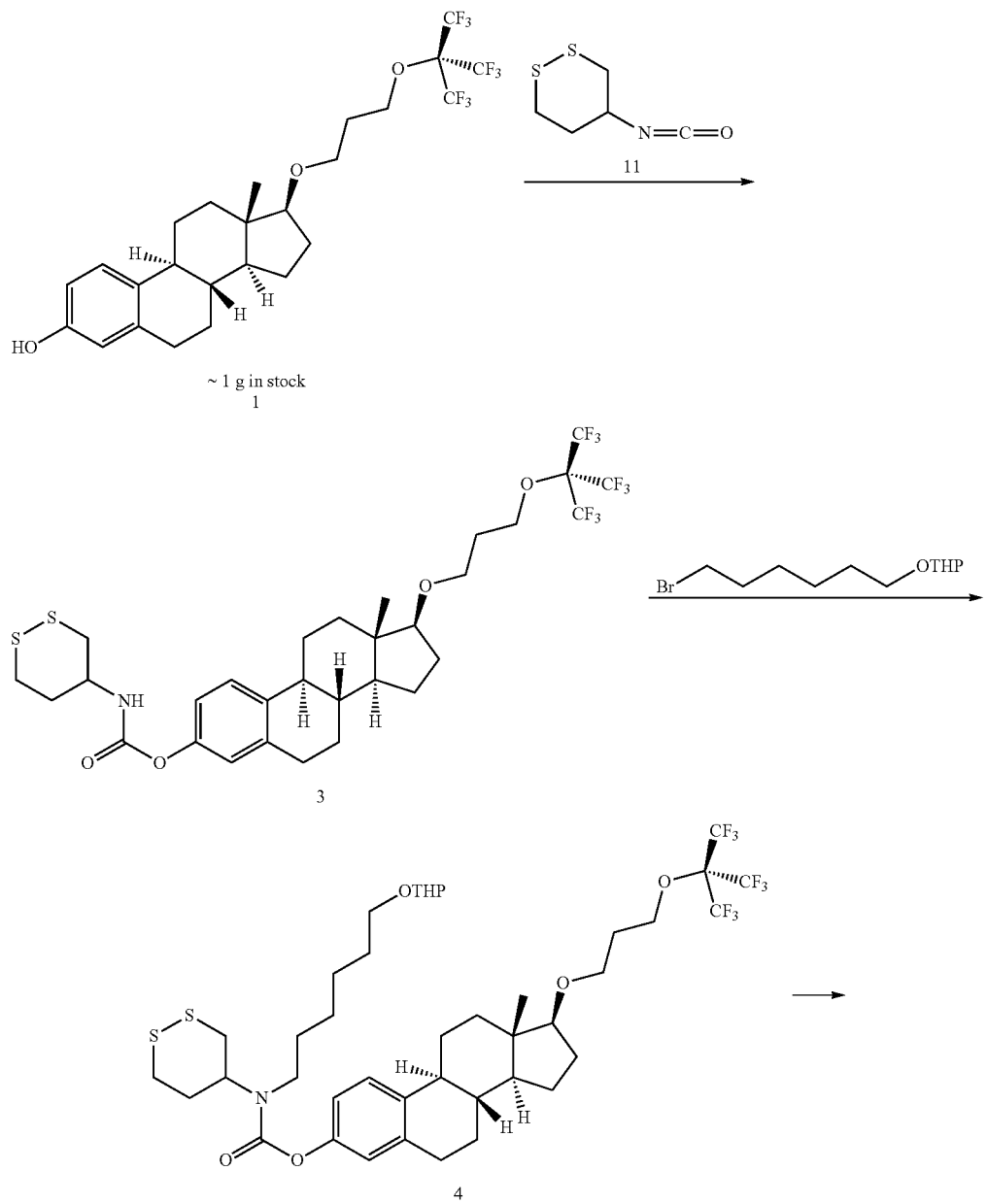

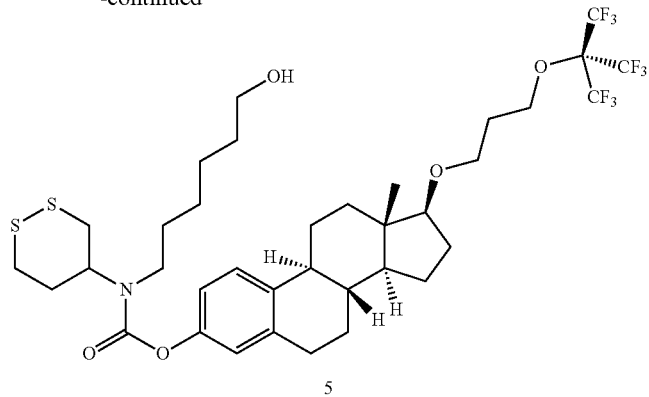
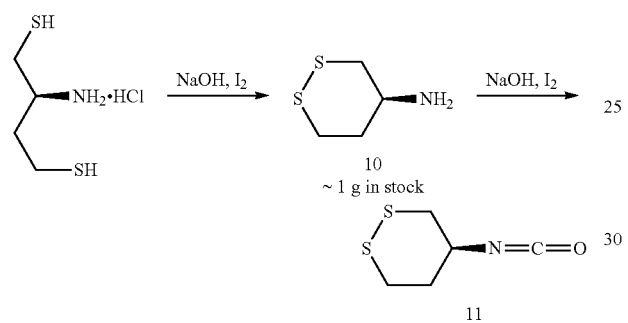
Scheme 2
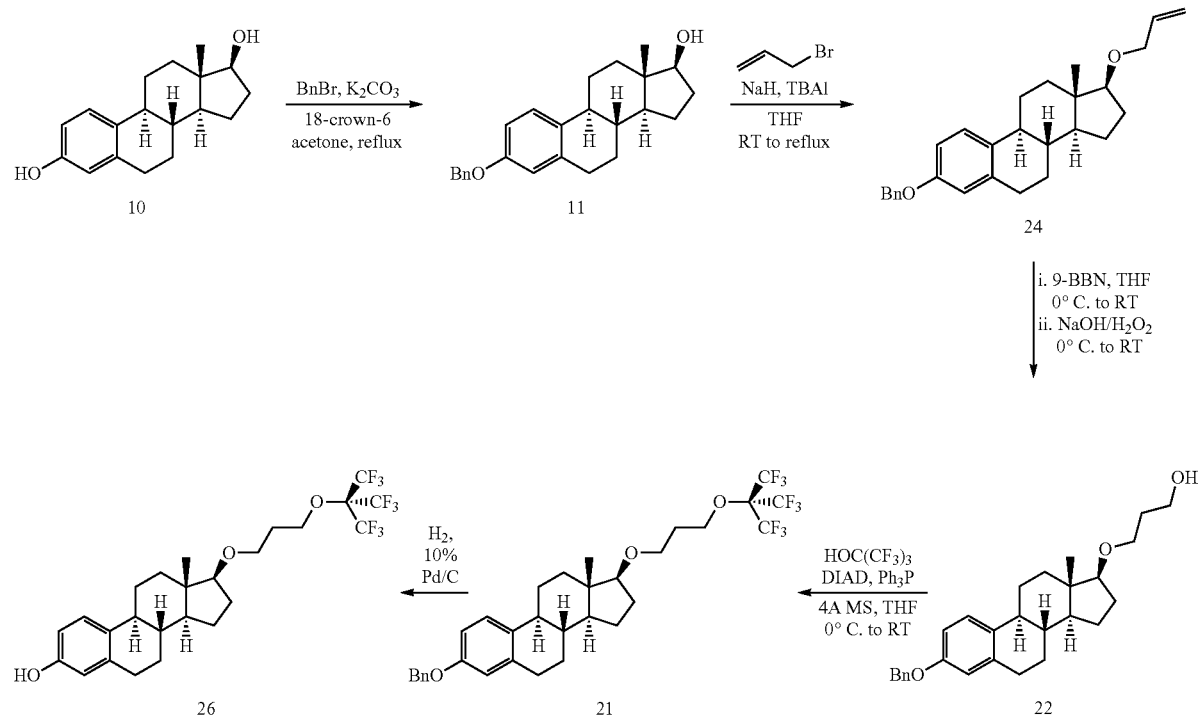
Scheme 3

Example 3: Proof-of-Concept: Molecular Cleavage of a Molecule of the Invention, Induced by Reductive Conditions Compound 5 includes a pro-drug according to the invention. It comprises a ROSS moiety according to Formula (III), and it has the following structure:

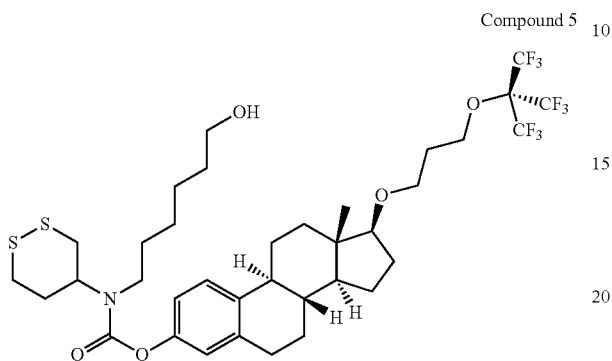

Compound 5

A DMSO solution of Compound 5 was incubated at room temperature for 24 hours. HPLC-MS revealed that the Compound is stable and intact. The Compound was then incubated at room temperature with one equivalent of the reducing agent tris (2-carboxyethyl) phosphine (TCEP). After 18 hours, HPLC-MS revealed four distinct peaks: (i). Intact Compound 5; (ii). a product corresponding to Compound 5 with two reduced thiol groups (Product 1); (iii). a product corresponding to cleaved Fragment A; and (iv). a product corresponding to cleaved Fragment B.

Product 1

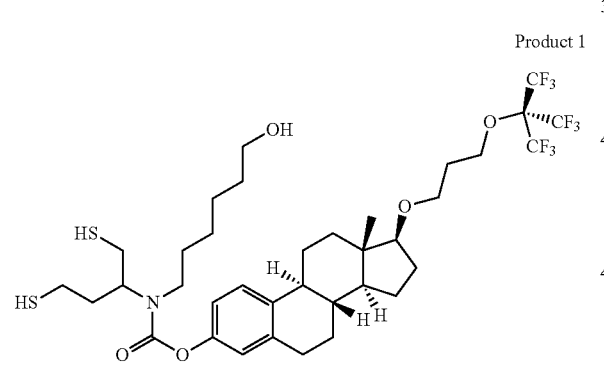

Cleaved Fragment A

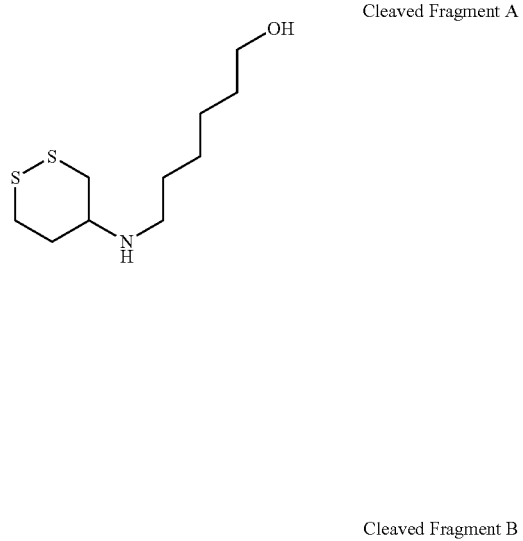

Cleaved Fragment B

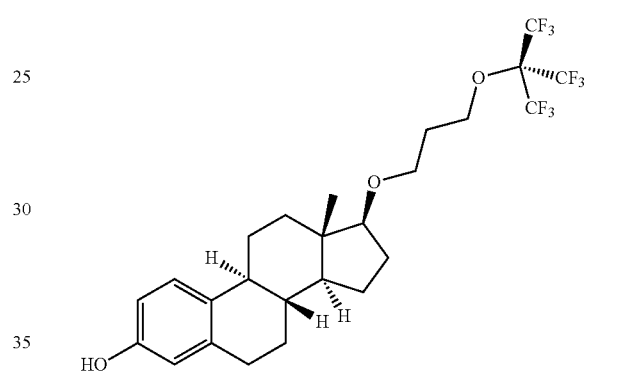

These results therefore demonstrate that in a non-reductive environment, the Compound of the invention is stable. However, in reductive conditions, conversion of the disulfide into free thiol groups takes place. Importantly, this step is evidently followed by an intramolecular reaction, with molecular cleavage at the carbamate moiety, conceivably related to nucleophilic attack on the respective carbonyl by a thiol or a thiolate group, conveniently located at the sixth atom position. Therefore, the Compound manifests selective reduction-dependent cleavage. The site of the nucleophilic attack is described in the following Scheme 4:

Scheme 4

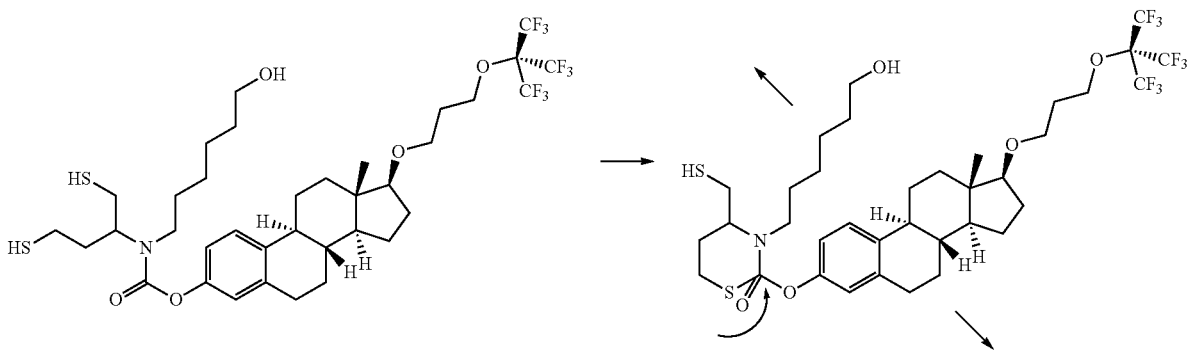

-continued

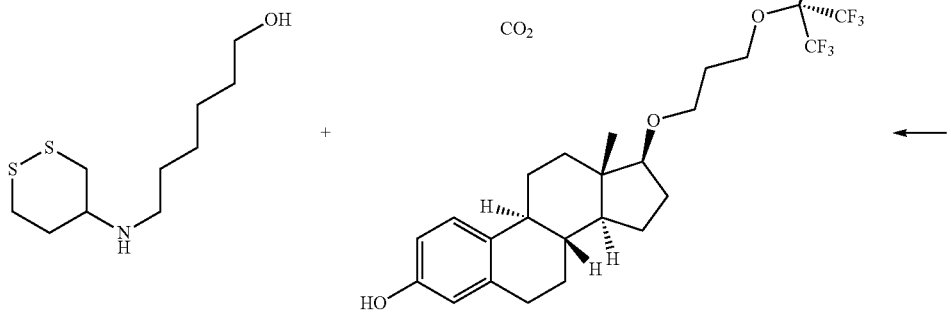

Example 4: Proof-of-Concept: Molecular Cleavage of a Molecule of the Invention, Induced by Reductive Conditions Compound A includes a pro-drug according to the invention. It comprises a ROSS moiety according to Formula (IIIb), and it has the following structure:

A

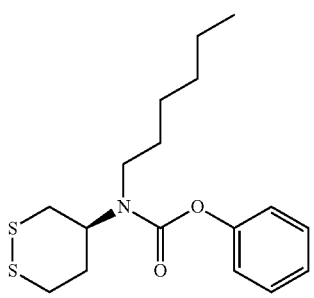

Compound A

Molecular Weight: 339.51

Dithiothreitol (DTT) is a reducing agent; once oxidized, it forms a stable six-membered ring, with an internal disulfide bond. Disulfide compound A was treated with excess dithiothreitol (15 equiv, aq. 0.5M, pH adjusted to 7 with phosphate buffer solution) in DMSO and phosphate buffer solution (pH 7) at 37° C. under an argon atmosphere. Two sets of samples were analyzed by HPLC/MS: at 6 and at 24 hours. After 6 hours, reduction of the disulphide bond (A2) was clearly visible.

A2

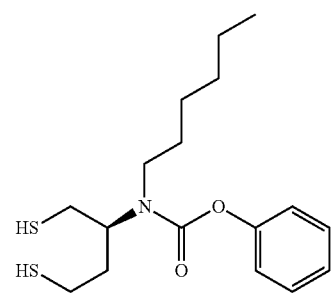

Molecular Weight: 341.53

Figure 4A:
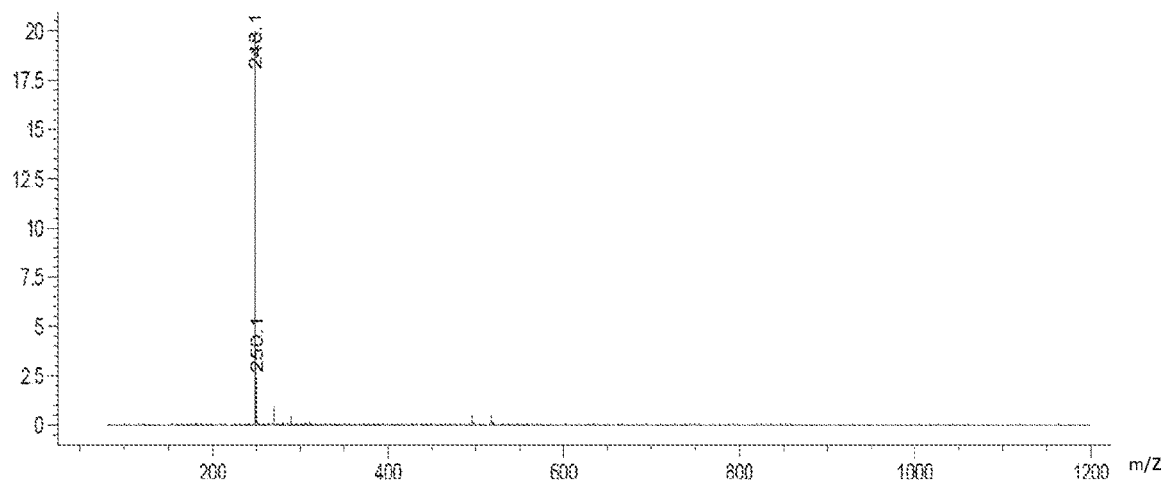
FIG. 4 describes progress of the reduction-induced cleavage process, using MS (mass spectroscopy) data after six hours (FIG. 4A) and 24 hours (FIG. 4B), clearly showing the formation of a new product at 2.080 min, with an m/z 248.1, corresponding to the mass of the reaction product, A3+1H.
Figure 4B:
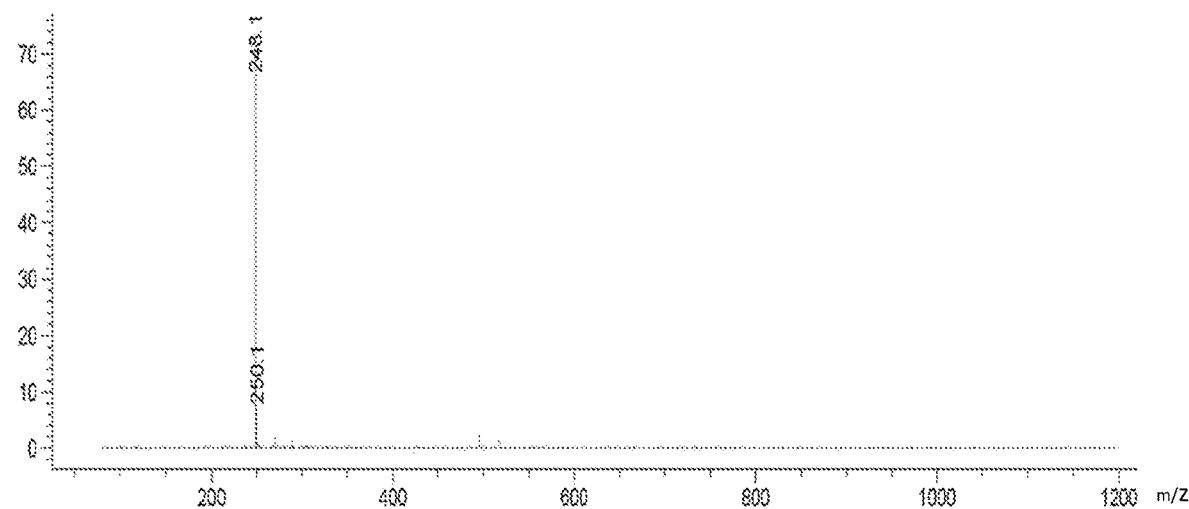

At both 6 hours and 24 hours, the analysis showed the formation of a new product at 2.080 min with an m/z 248.1, corresponding to the mass of A3+1H (See FIGS. 4A and 4B, with the corresponding MS data). These results confirm, that subsequent to reduction of the disulfide bond, cleavage of Compound A, to release the phenol moiety, and the respective cyclic adduct A3 was generated. As expected, the peak at 24 hours was of larger amplitude (70% vs. 30%).

A3

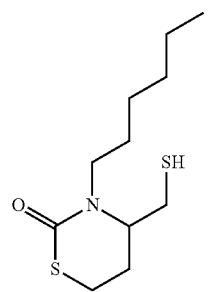

Molecular Weight: 247.42

Example 5: Proof-of-Concept: Molecular Cleavage of a Molecule of the Invention, Induced by Reductive Conditions Compound B is a pro-drug according to the invention, similar to the Compound of Examples 3 and 4, but with a fluorine atom on the aromatic ring. This acts to lower the pKa of the phenol group by approximately 1.3 units, making it a markedly better leaving group. Compound B comprises a ROSS moiety according to Formula (IIIa), and it has the following structure:

Compound B

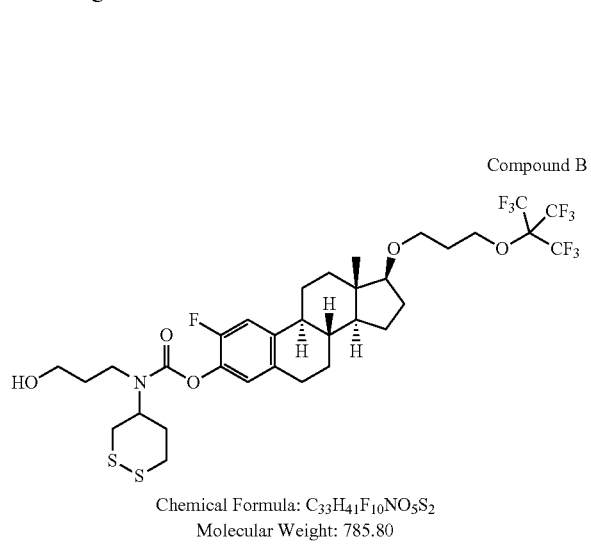

Chemical Formula: $C_{33}H_{41}F_{10}NO_5S_2$
Molecular Weight: 785.80

The experiment comprised incubation of Compound B with 100 equivalents of the reducing agent DTT (0.1 mL of 2 M solution), 1.0 mL DMSO in aqueous buffer (pH=7.0), at 37° C. under argon atmosphere. Three sets of samples were analyzed by HPLC/MS: at 1 hour, 6 hours, and at 24 hours. Already after one hour, reduction of the disulphide bond of Compound B was clearly evident, with evidence for a full conversion of Compound B to Compound B2. This structure was thereafter maintained throughout the experiment.

Compound B2

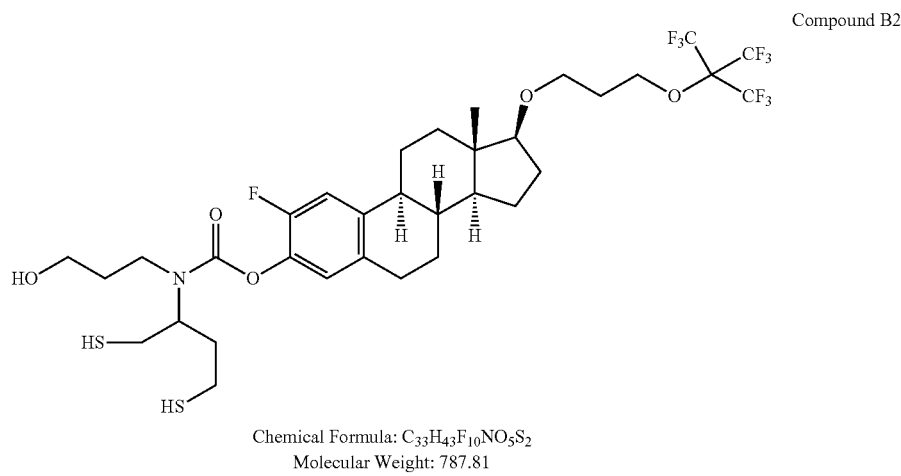

Chemical Formula: $C_{33}H_{43}F_{10}NO_5S_2$
Molecular Weight: 787.81

Importantly however, HPLC/MS also indicated the formation of Compound B3, indicating cleavage of Compound B2, at the carbamate bond, with release of the phenolic moiety, Compound B3:

Compound B3

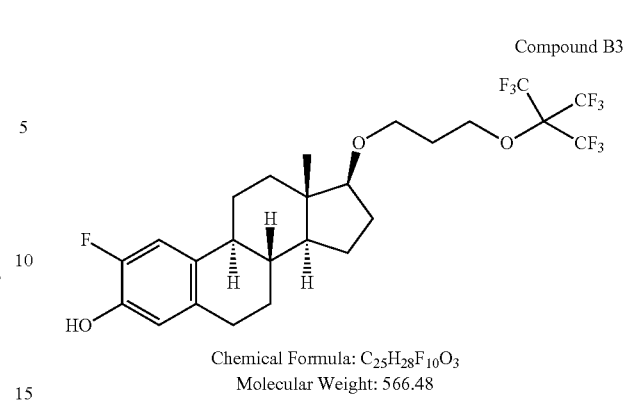

Chemical Formula: $C_{25}H_{28}F_{10}O_3$
Molecular Weight: 566.48

There was evidence for such cleavage, with release of Compound B3, already at one hour of incubation, where 30% cleavage was detected. This increased to 90% of cleaved product at 6 hours, and full cleavage by 24 hours. These experimental data therefore demonstrate the activity of the reduction-induced cleavage mechanism of the Invention, and also its amenability to structural/functional optimizations, as exemplified here by the insertion of the aromatic fluorine atom: by improving the quality of phenol as a leaving group by lowering its pKa, enhanced cleavage efficacy was observed: while the phenol of Example 4 provided 30% and 70% cleavage at 6 and 24 hours respectively, the addition of the aromatic fluorine atom enabled 30% cleavage at one hour, and 90% cleavage at 6 hours, with practical full cleavage by 24 hours.

Figure 5:
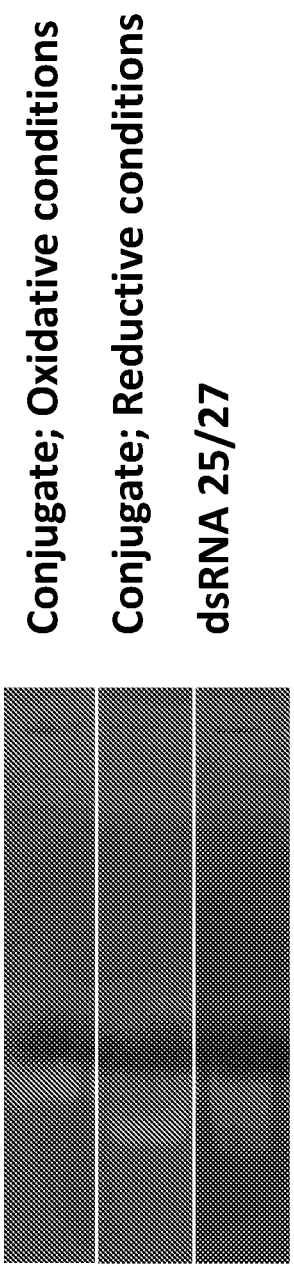
FIG. 5 presents a gel illustrating cleavage of Compound B of the Invention in reductive conditions.

Example 6: Proof-of-Concept: Molecular Cleavage of a Molecule of the Invention (Compound B) Induced by Reductive Conditions In Vitro In order to detect cleavage of Compound B, a double-stranded 25-27 RNA (19 picomol) (Dicer substrate designed to silence the EGFP gene), conjugated at each 5'-end to Compound B, was exposed to 10 mM DTT (Dithiothreitol) for 10 minutes at 95° C. Reaction mixture was then subjected to native poly acrylamide gel electrophoresis, followed by staining with ethidium bromide, in order to visualize the RNA molecules in the mixture. The same a double-stranded 25-27 RNA, un-conjugated to Compound B was exposed to identical conditions, and served as Control. Another Control was the Compound B Conjugate, not exposed to the reductive conditions. As seen in the FIG. 5, Compound B was selectively cleaved in the reductive conditions, but not in the non-reductive conditions, generating a band at the same height as the non-conjugated ds-RNA.

The invention claimed is:

1. A method for redox-dependent cleavage of a Pro-drug, said method comprising (A) incorporation of a ROSS red-ox sensitive switch moiety in the structure of the Pro-drug, wherein said red-ox sensitive switch moiety ROSS has the following structural motifs: (i) a cyclic hydrocarbon disulfide moiety; (ii) a carbonyl group, positioned at 5-7 atoms from at least one of the sulfur atoms; and (iii) a leaving group, attached to the carbonyl group through carbamate, ester or amide bonds; (B) maintaining the Pro-drug initially in an oxidative environment; and (C) transferring the Pro-drug into an ambient reductive environment; Wherein said red-ox sensitive switch moiety has the general Formula (Ia) or Formula (Ib):

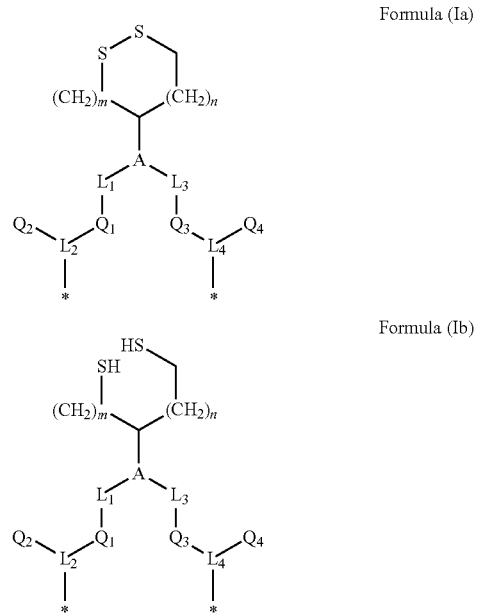

Formula (Ia)

Formula (Ib)

wherein:
m and n, each stands for an integer, independently selected from 1, 2, 3 or 4;
A is selected from null; —CH—, —N—, —CH$_2$—CH—; —CH$_2$—N—; —NH—CH—; —S—CH—; —O—CH—;
$Q_1$, $Q_2$, $Q_3$ or $Q_4$ may be the same or different, and are each independently selected from null, hydrogen, hydroxyl, amine group, a nitro group, a sulfonyl group, a halogen atom, a fluorocarbon group; a carbonyl group C(=O)—; an amide group [—C(=O)—NH—; —HN—C(=O)—]; —O—C(=O); —C(=O)—O—; a thioester group [—C(=O)—S—; —S—C(=O)—]; a thionoester group —O—C(=S); —C(=S)—O—;
wherein if $Q_1$ is hydrogen, hydroxyl, a nitro group, a sulfonyl group, a halogen atom, a fluorocarbon group, then $Q_3$ is different from any one of hydrogen, hydroxyl, a nitro group, a sulfonyl group, a halogen atom, a fluorocarbon group; and wherein if $Q_3$ is hydrogen, hydroxyl, a nitro group, a sulfonyl group, a halogen atom, or a fluorocarbon group, then $Q_1$ is different from any one of hydrogen, hydroxyl, a nitro group, a sulfonyl group, a halogen atom, a fluorocarbon group;

$L_1$, $L_2$, $L_3$ and $L_4$ may be the same or different, and are each independently selected from null, or from the group consisting of:
linear, cyclic or branched $C_1$, $C_2$, $C_3$, $C_4$, $C_5$ alkyl or hetero-alkyl;
linear, cyclic or branched $C_2$, $C_3$, $C_4$, $C_5$, $C_6$, alkylene or heteroalkylene; and
$C_5$, $C_6$, $C_7$, $C_8$, $C_9$, $C_{10}$ aryl or heteroaryl;
and wherein if $L_2$ is null, then $L_4$ is not null; and if $L_4$ is null then $L_2$ is not null; * is an optional attachment point of chemical moieties Y and Z, wherein the Pro-drug may include Y, Z or both, and wherein Y and Z each being a subunit of the pro-drug, destined to be separated and released upon its cleavage; and wherein Y and Z may be identical or different;
thereby providing the required conditions for ring opening, cleavage of the pro-drug, and release of the active drug.

2. A method for redox-dependent cleavage of a Pro-drug, said method comprising (A) incorporation in the structure of the Pro-drug a red-ox sensitive switch moiety ROSS according to any of selected from:

Formula (IIa)

Formula (IIb)

Formula (III)

Formula (IIIa)

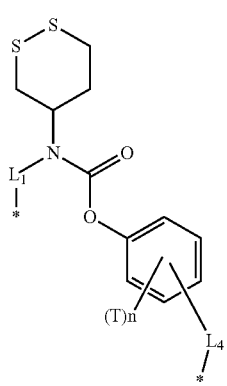

Formula (IIIb)

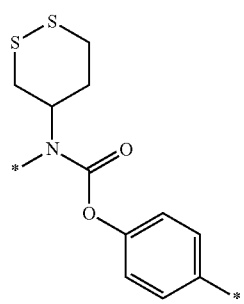

Formula (IV)

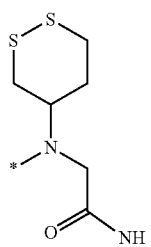

Formula (V)

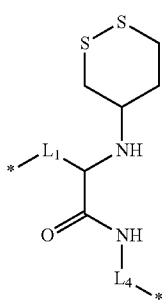

Formula (VI)

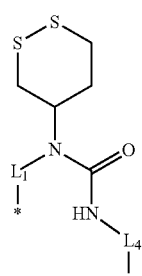

Formula (VII)

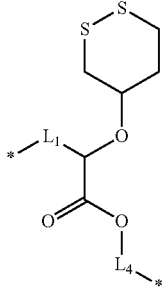

A is selected from null; —CH—, —N—, —CH$_2$—CH—; —CH$_2$—N—; —NH—CH—; —S—CH—; —O—CH—;

$Q_1$, $Q_2$, $Q_4$ or $Q_4$ may be the same or different, and are each independently selected from null, hydrogen, hydroxyl, amine group, a nitro group, a sulfonyl group, a halogen atom, a fluorocarbon group; a carbonyl group —C(=O)—; an amide group [—C(=O)—NH—; —HN—C(=O)—]; —O—C(=O); —C(=O)—O—; a thioester group [—C(=O)—S—; —S—C(=O)—]; a thionoester group —O—C(=S); —C(=S)—O—;

wherein if $Q_1$ is hydrogen, hydroxyl, a nitro group, a sulfonyl group, a halogen atom, a fluorocarbon group, then $Q_3$ is different from any one of hydrogen, hydroxyl, a nitro group, a sulfonyl group, a halogen atom, a fluorocarbon group; and wherein if $Q_3$ is hydrogen, hydroxyl, a nitro group, a sulfonyl group, a halogen atom, or a fluorocarbon group, then $Q_1$ is different from any one of hydrogen, hydroxyl, a nitro group, a sulfonyl group, a halogen atom, a fluorocarbon group;

$L_1$, $L_2$, $L_3$ and $L_4$ may be the same or different, and are each independently selected from null, or from the group consisting of:

linear, cyclic or branched $C_1$, $C_2$, $C_3$, $C_4$, $C_5$ alkyl or hetero-alkyl;

linear, cyclic or branched $C_2$, $C_3$, $C_4$, $C_5$, $C_6$, alkylene or heteroalkylene; and $C_5$, $C_6$, $C_7$, $C_8$, $C_9$, $C_{10}$ aryl or heteroaryl;

and wherein if $L_2$ is null, then $L_4$ is not null; and if $L_4$ is null then $L_2$ is not null;

* is an optional attachment point of chemical moieties Y and Z, wherein the Pro-drug may include Y, Z or both, and wherein Y and Z each being a subunit of the pro-drug, destined to be separated and released upon its cleavage; and wherein Y and Z may be identical or different;

(B) maintaining the Pro-drug initially in an oxidative environment; and (C) transferring the Pro-drug into an ambient reductive environment.

* * * * *